(12) United States Patent
Kratzer et al.

(10) Patent No.: US 12,014,332 B2
(45) Date of Patent: *Jun. 18, 2024

(54) SYSTEMS AND METHODS FOR DETERMINING A LENS PRESCRIPTION

(71) Applicant: Carl Zeiss Vision GmbH, Aalen (DE)

(72) Inventors: Timo Kratzer, Aalen (DE); Herbert Krug, Aalen (DE); Jesús-Miguel Cabeza-Guillén, Aalen (DE); Harald Ruenz, Essingen (DE)

(73) Assignee: Carl Zeiss Vision GmbH, Aalen (DE)

( * ) Notice: Subject to any disclaimer, the term of this patent is extended or adjusted under 35 U.S.C. 154(b) by 4 days.

This patent is subject to a terminal disclaimer.

(21) Appl. No.: 18/047,686

(22) Filed: Oct. 19, 2022

(65) Prior Publication Data

US 2023/0062220 A1    Mar. 2, 2023

Related U.S. Application Data

(63) Continuation of application No. 13/685,324, filed on Nov. 26, 2012, now Pat. No. 11,521,174, which is a continuation of application No. 12/185,524, filed on Aug. 4, 2008, now abandoned.

(51) Int. Cl.
  G06Q 10/10      (2023.01)
  G16H 20/10     (2018.01)
  G16H 40/67     (2018.01)
(52) U.S. Cl.
  CPC .............. G06Q 10/10 (2013.01); G16H 20/10 (2018.01); G16H 40/67 (2018.01)

(58) Field of Classification Search
  CPC .... G06Q 10/10; G06Q 30/0621; G06Q 50/22; G16H 20/10; G16H 40/67
  See application file for complete search history.

(56) References Cited

U.S. PATENT DOCUMENTS

| 4,105,302 | A   | 8/1978  | Tate |
| 6,294,999 | B1  | 9/2001  | Yarin et al. |
| 6,382,795 | B1  | 5/2002  | Lai |
| 6,406,146 | B1  | 6/2002  | Lai |
| 6,499,843 | B1* | 12/2002 | Cox ..................... A61B 3/0025 |
|           |     |         | 351/246 |

(Continued)

FOREIGN PATENT DOCUMENTS

| CN | 1612714 A | 5/2005 |
| CN | 1826080 A | 8/2006 |

(Continued)

OTHER PUBLICATIONS

A. Bellissimo et al.: "Secure Software Updates: Disappointments and New Challenges," HotSec '06: 1st USENIX Workshop on Hot Topics in Security, 2006.

(Continued)

*Primary Examiner* — Eliza A Lam
(74) *Attorney, Agent, or Firm* — Tautz & Schuhmacher LLC; Georg M. Hasselmann

(57) ABSTRACT

Methods for dispensing eyeglasses are disclosed. The methods involve making a subjective refraction and an objective refraction and sending the information to a calculation computer to combine both refractions to calculate the person's prescription. The person's prescription is subsequently sent to a manufacturing location separate from the calculation computer for manufacture of the lenses.

20 Claims, 6 Drawing Sheets

(56) References Cited

U.S. PATENT DOCUMENTS

| | | | |
|---|---|---|---|
| 6,511,180 B2 | 1/2003 | Guirao et al. | |
| 6,533,418 B1 * | 3/2003 | Izumitani | G02C 13/003 351/204 |
| 6,575,572 B2 | 6/2003 | Lai et al. | |
| 6,997,555 B2 | 2/2006 | Dick et al. | |
| 7,084,986 B2 | 8/2006 | Hellmuth et al. | |
| 7,168,807 B2 | 1/2007 | Chernyak et al. | |
| 7,188,082 B2 | 3/2007 | Keane et al. | |
| 7,287,853 B2 | 10/2007 | Toshima et al. | |
| 7,441,895 B2 * | 10/2008 | Akiyama | G02C 13/005 351/178 |
| 7,731,363 B2 | 6/2010 | Chernyak et al. | |
| 7,744,214 B2 | 6/2010 | Blum et al. | |
| 8,079,707 B2 | 12/2011 | Cabeza et al. | |
| 2004/0046287 A1 | 3/2004 | Andino et al. | |
| 2008/0100800 A1 | 5/2008 | Guillen et al. | |
| 2010/0030570 A1 | 2/2010 | Kratzer et al. | |
| 2013/0090944 A1 | 4/2013 | Kratzer et al. | |

FOREIGN PATENT DOCUMENTS

| | | |
|---|---|---|
| CN | 101059871 A | 10/2007 |
| CN | 201689461 U | 12/2010 |
| EP | 1154302 A1 | 11/2001 |
| EP | 1324689 B1 | 8/2006 |
| WO | 2008049503 A2 | 5/2008 |

OTHER PUBLICATIONS

International Search Report and Written Opinion by the International Searching Authority in PCT/EP2009/005507, which is a counterpart hereof, mailed Oct. 30, 2009.

English-language translation of Chinese Office Action for CN 200980130407.3, which is a counterpart hereof, dated Feb. 2, 2012.

Office action by the European Patent Office Action for EP 09 777 531.6-2319, which is a counterpart hereof, dated May 3, 2012 (in English).

Decision on Rejection of the Chinese Patent Office for CN 200980130407.3, which is a counterpart hereof, dated Jul. 23, 2012, and English-language translation thereof.

Office action by the European Patent Office for EP 09 777 531.6-1660, which is a counterpart hereof, dated Jan. 21, 2014 (in English).

Extended European Search Report by the European Patent Office for EP 13 005 579.1, which is a counterpart hereof, dated Apr. 23, 2014 (in English).

Reexamination Decision revoking the Decision on Rejection for CN Appl No. 200980130407.3, which is a counterpart hereof, dated Apr. 30, 2014, and English-language translation thereof.

Office action by the European Patent Office for EP 09 777 531.6, which is a counterpart hereof, dated Aug. 12, 2014 (in English).

Office action by the the Chinese Patent Office for CN 200980130407. 3, which is a counterpart hereof, dated Sep. 2, 2014, and English-language translation thereof.

Decision on Rejection of the Chinese Patent Office in CN 200980130407.3, which is a counterpart hereof, dated Dec. 29, 2015, and English-language translation thereof.

English-language translation of the Bill of Defence by the Chinese Patent Office in CN 200980130407.3, which is a counterpart hereof, dated Jul. 29, 2016.

Office action of the European Patent Office for EP 13 005 579.1, which is a counterpart hereof, dated Dec. 2, 2016 (in English).

Office action of the Chinese Patent Office for CN 2016101850888, which is a counterpart hereof, dated Dec. 18, 2017, and English-language translation thereof.

Office action of the Indian Patent Office for In 7789/DELNP/2010, which is a counterpart hereof, dated Aug. 29, 2018 (in Hindi and English).

Office action of the Chinese Patent Office for CN 2016101850888, which is a counterpart hereof, dated Aug. 30, 2018, and English-language translation thereof.

Office action of the Chinese Patent Office for CN 2016101850888, which is a counterpart hereof, dated Dec. 3, 2018, and English-language translation thereof.

Office action of the Chinese Patent Office for CN 2016101850888, which is a counterpart hereof, dated Mar. 11, 2019, and English-language translation thereof.

Notice of Reexamination by the Chinese Patent Office for CN 2016101850888, which is a counterpart hereof, dated Aug. 26, 2020, and English-language translation thereof.

* cited by examiner

SYSTEMS AND METHODS FOR DETERMINING A LENS PRESCRIPTION

CROSS REFERENCE TO RELATED APPLICATIONS

This application is a continuation application of U.S. patent application Ser. No. 13/685,324, now U.S. patent application publication 2013/0090944 A1, filed Nov. 26, 2012, which is a continuation of U.S. patent application Ser. No. 12/185,524, now abandoned, filed Aug. 4, 2008, and the entire content of both applications is incorporated herein by reference.

BACKGROUND

Eye care professionals (ECPs), such as opticians, optometrists, ophthalmologists, and eye doctors, typically dispense eye glasses to people based on a study of the person's vision that involves taking a medical history of the person's vision and a subjective refraction to get the person's prescription. After the person selects eyeglass frames, the ECP usually measures the centration of the frame for the person and orders lenses for the frame based on the person's prescription and the centration measurement.

SUMMARY

Methods for dispensing eyeglasses are disclosed.

In some aspects, the methods involve making a subjective refraction and sending the information from the subjective refraction to a calculation computer to calculate the person's prescription. The person's prescription is sent to a manufacturing location separate from the calculation computer for manufacture of the lenses.

In some additional aspects, the methods involve making a subjective refraction and an objective refraction and sending the information from the subjective and objective refractions to a calculation computer to calculate the person's prescription. The person's prescription is sent to a manufacturing location separate from the calculation computer for manufacture of the lenses. Making the objective refraction may involve making a wavefront measurement of one or both of the person's eyes and calculating the person's prescription may involve using the wavefront measurement to calculate the person's prescription.

In some additional aspects, methods for dispensing eyeglasses can involve providing a communication link between a computer located at an eye care professional's office and a calculation computer located elsewhere. The method can include determining a prescription based on information gathered by the eye care professional and sent to the calculation computer. The method can also involve placing an order for eye glass lenses by sending information to a manufacturing computer in a location separate from the calculation computer. In this method, the calculations used to determine the prescription for the lenses are performed at a location separate from the manufacturing location.

In general, in one aspect, the disclosure features a method that includes making a subjective refraction and an objective refraction of a person to determine information about the person's vision. The method also includes entering the information about person's vision based on the subjective refraction and the objective refraction into a first computer system. The method also includes sending the information about the person's vision to a second computer system, the second computer system being configured to perform calculations based on information about the person's vision and generate prescription information. The second computer is in a separate location from the first computer. The method also includes receiving, at the first computer from the second computer, the prescription information. The method also includes placing an order for a lens based on the prescription information by sending the prescription information from the first computer to a third computer associated with a lens manufacturing site. The third computer is in a separate location from the first computer and the second computer.

In general, in another aspect, the disclosure features a method that includes receiving, at a second computer from a first computer, information about a person's vision including subjective refraction information and objective refraction information. The second computer is in a separate location from the first computer and in a separate location from a third computer associated with a lens manufacturing site. The method also includes performing, using the second computer, calculations to generate a lens prescription based on the information about the person's vision. The method also includes sending the revised lens prescription to the first computer.

In general, in an additional aspect, the disclosure features a method that includes making a subjective refraction of a person to determine information about the person's vision. The method also includes making a wavefront measurement of one or both of the person's eyes to determine information about the optical properties of one or both of the person's eyes. The method also includes sending the information about the person's vision and the information about the optical properties of one or both of the person's eyes from an ordering computer in the eye care processional's office to a calculation computer located in a location separate from the eye care professional's office. The method also includes receiving, at the ordering computer, prescription information from the calculation computer. The method also includes ordering eyeglass lenses based on the prescription by sending the prescription information to a manufacturing computer.

Embodiments can include one or more of the following.

The first computer can be an ordering computer. The second computer can be a calculation computer. The third computer can be a manufacturing computer. The ordering computer calculation computer and manufacturing computer can each be located in a different location.

Multiple ordering computers can be connected to a single calculation computer. Multiple ordering computers can be connected to a manufacturing location.

The objective refraction can be derived from a wavefront measurement of one or both of the person's eyes that determines information about the optical properties of one or both of the person's eyes.

The objective refraction can be derived from a ray tracing method of one or both of the person's eyes that determines information about the optical properties of one or both of the person's eyes.

The objective refraction can be derived from a tomographic method of one or both of the person's eyes determining information about the optical properties of one or both of the person's eyes.

The objective refraction can be derived from a corneal topography method of one or both of the person's eyes determining information about the optical properties of one or both of the person's eyes corneas.

The method can also include sending the lens prescription from the first computer to the third computer.

In some aspects, a system includes an input interface configured to input information about a person's vision determined on the basis of a subjective refraction. The system also includes a device configured to obtain information about a person's vision determined on the basis of an objective refraction. The system also includes a calculating device configured to calculate a prescription for the person based on the information about the person's vision determined by subjective refraction and based on the information about the person's vision determined by objective refraction. The system also includes an outputting interface configured to output the prescription, wherein the calculation device is located in a separate location from the input interface, the output interface, and a manufacturing location.

The details of one or more embodiments are set forth in the accompanying drawings and the description below. Other features and advantages will be apparent from the description, drawings, and claims.

BRIEF DESCRIPTION OF THE DRAWINGS

Like reference symbols in the various drawings indicate like elements.

DESCRIPTION OF EXEMPLARY EMBODIMENTS

Figure 1:
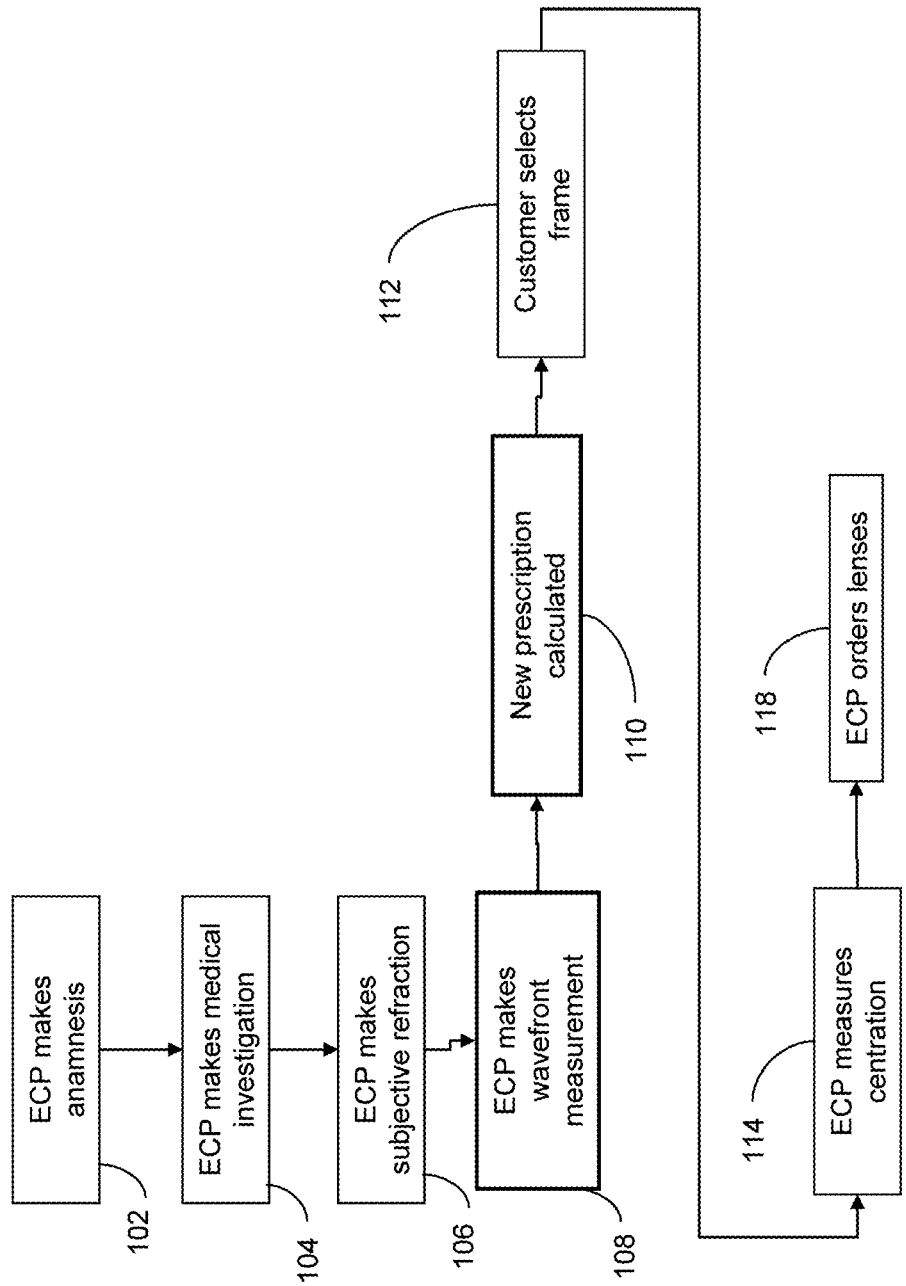
FIG. 1 is a flow chart showing a procedure for determining an eyeglass prescription and ordering lenses.

Referring to FIG. 1, a procedure 100 for obtaining an eyeglass prescription and ordering eyeglass lenses for a person includes making an anamnesis 102 and medical investigation 104 of the person, followed by a subjective refraction 106 and an objective refraction measurement 108. For example, the ECP can make a wavefront measurement. The eye care professional (ECP) determines the person's prescription 110 based on the results of subjective refraction 106 and wavefront measurement 108. After the person selects eyeglass frames 112, the ECP optional measures a centration 114 of the frames and orders the lenses 118 from a lens maker (e.g., from a third party lens maker or an in-house lens maker) according to the prescription and centration measurement.

Figure 2:
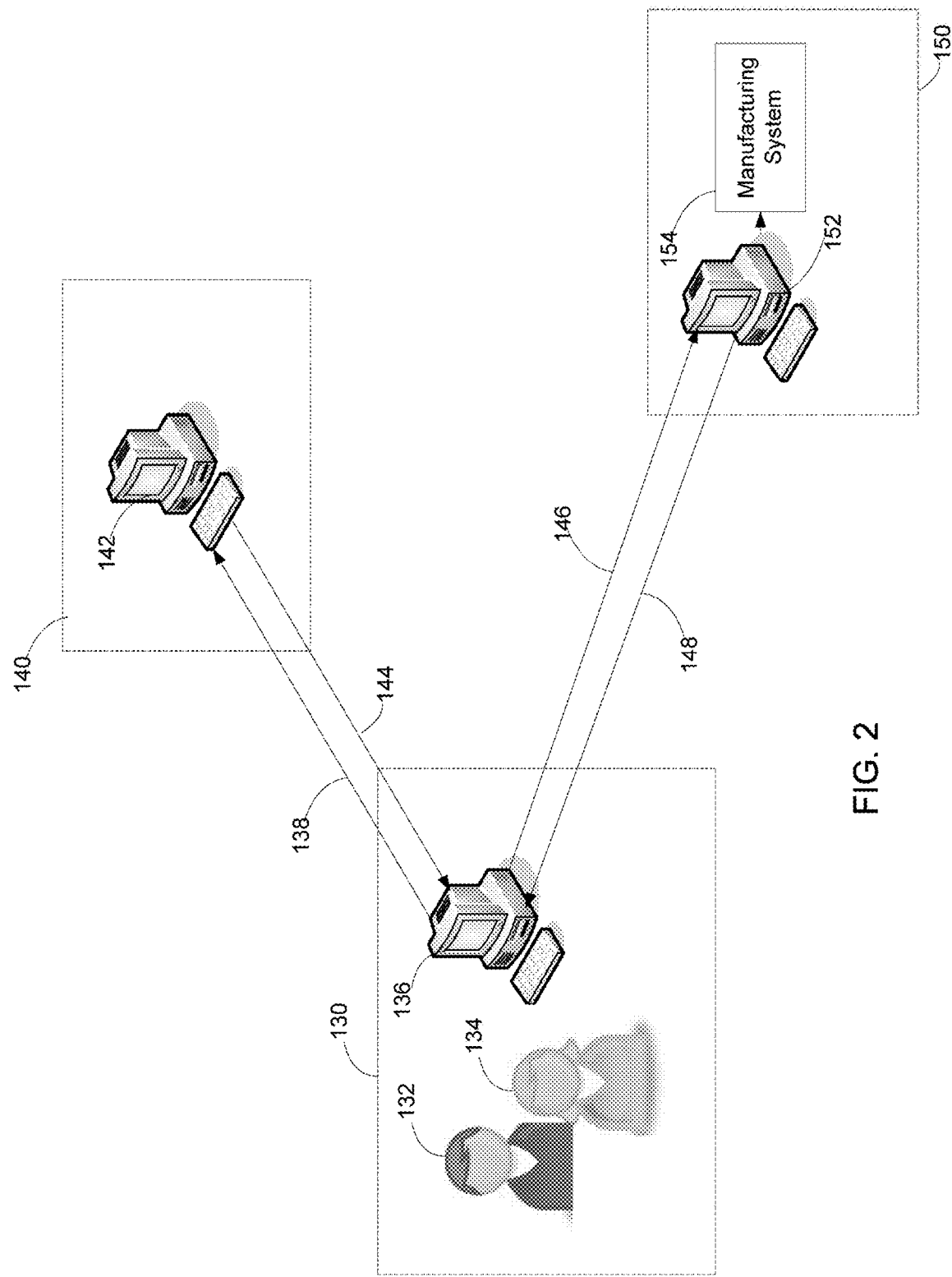
FIG. 2 is block diagram of a multi-computer system.

The various portions of procedure 100 for obtaining an eyeglass prescription and ordering eyeglass lenses for a person occur in multiple locations. For example, FIG. 2 shows an arrangement that includes an ordering location 130 that includes an ordering computer 136, a calculation location 140 that includes a calculation computer 142, and a manufacturing location 150 that includes a manufacturing computer 152. The ordering computer 136, calculation computer 142, and manufacturing computer 152 are in electronic communication and transmit data used to determine the eyeglass prescription and place the order for the eyeglass lenses. The ordering location 130, calculation location 140, and manufacturing location 150 can be physically separate locations (e.g., located in separate buildings) and/or can be separate systems located within a single facility.

The interactions between the ECP 132 and person 134 (e.g., making anamnesis 102, performing the medical investigation 104, performing subjective refraction 106 measurements, and performing a wavefront measurement 108) occur at the ordering location 130, for example at the ECP's office or other facility (as described in more detail below). At the ordering location 130, the ECP 132 enters the information obtained during the interaction between the ECP 132 and person 134 into the ordering computer 136 and transmits the information to the calculation computer 142 (as indicated by arrow 138). The calculation computer 142 performs calculations based on the information received from the ordering computer 136 and generates information relevant for the selecting and/or manufacturing the lens such as prescription information, lens thickness, information related to manufacturability, and/or an estimated cost of the lens. The calculation computer 142 sends the information to the ordering computer 136 (as indicated by arrow 144). The process of sending information to the calculation computer 142 and receiving information relevant for the manufacturing of the lens can be an iterative process. For example, if the ECP 132 is not satisfied with the calculated prescription or other information related to the lenses, the ECP 132 revises the data and sends the revised data to the calculation computer 142 to generate revised prescription data. When the ECP 132 is satisfied with the prescription, the prescription and other information relevant for the manufacturing of the lens are sent from the ordering computer 136 to the manufacturing computer 152 (as indicated by arrow 146) and the manufacturing computer 152 sends a confirmation of the order to the ordering computer 136 (as indicated by arrow 148). Due to the dispersed nature of this arrangement, all calculations to determine the prescription based on the wavefront data and other information provided by the ECP are performed in a location separate from the manufacturing location 150.

It is believed that performing the calculations to generate the lens prescription at a calculation computer 142 that is separate from the ordering computer 136 and the manufacturing computer 152 provides various advantages. For example, in some embodiments, performing the calculations at a location separate from the manufacturing site can reduce the amount of data transferred to the manufacturing site (e.g., the wavefront data is not sent to the manufacturing computer). If existing ordering systems associated with a particular manufacturing site do not include fields for providing wavefront data, performing the calculations at a separate location prior to sending the information to the manufacturing site can allow a prescription to be ordered using the existing ordering systems that accounts for the wavefront data. For example, some manufacturing locations may not have the capability to use wavefront data to determine a prescription. By performing the calculations at a separate location and sending a prescription that already accounts for the wavefront data, the manufacturing locations can generate lenses having prescriptions based on wavefront data without having to upgrade the manufacturing locations to perform such calculations. In addition, since the prescription is determined prior to placing the order at the manufacturing location, the ECP can review and adjust the prescription prior to placing the order.

Figure 3:
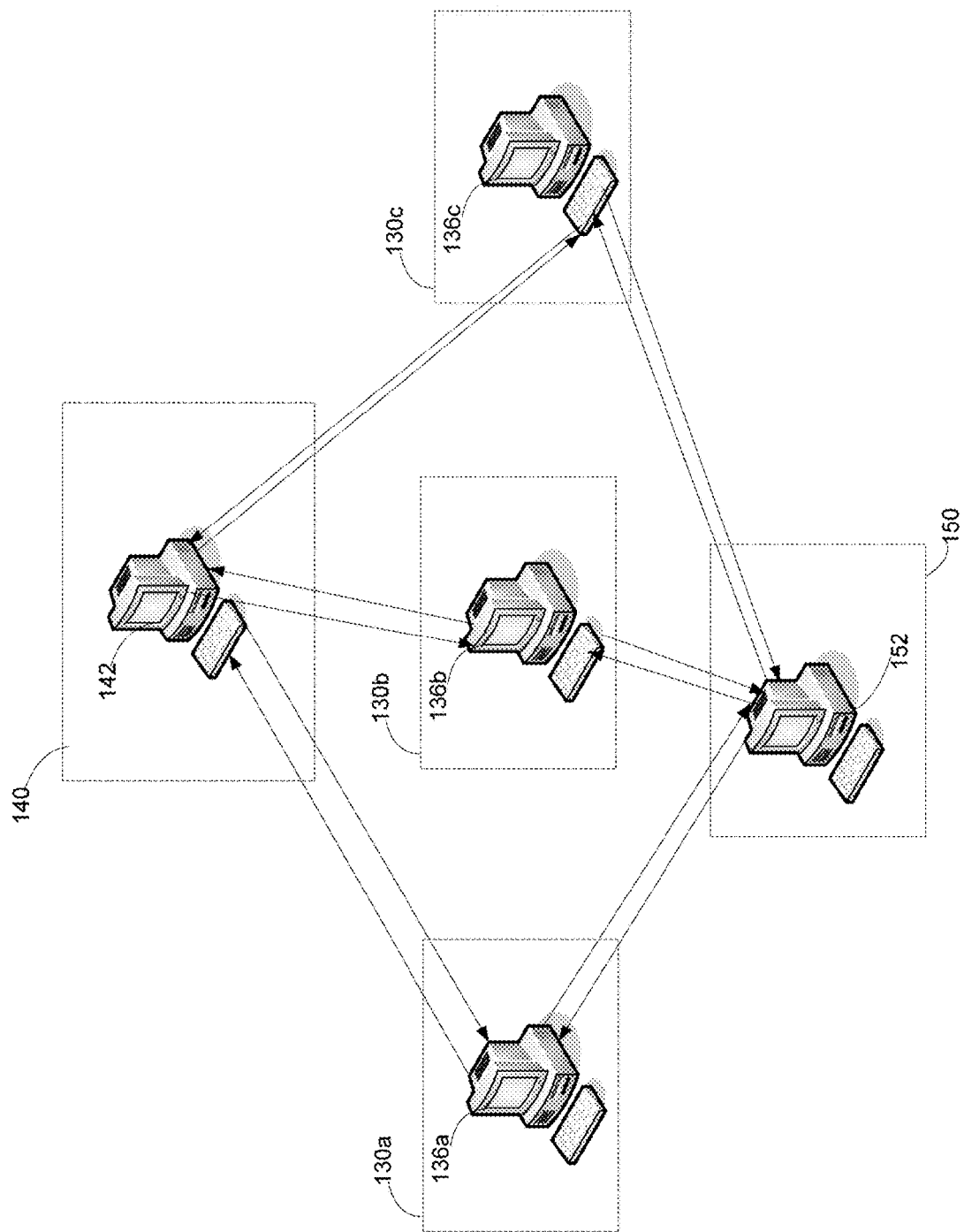
FIG. 3 is block diagram of a multi-computer system.

In another example, as shown in FIG. 3, in some embodiments, performing the calculations at a calculation computer 142 that is separate from the ordering computer 136 and the manufacturing computer 152 allows multiple ordering computers 136a, 136b, 136c to send data to a central calculation computer 142 that performs the calculations to determine the prescriptions. By having multiple ordering computers 136a, 136b, 136c using the same central calculation computer 142, the amount of software and data needed by the ordering computers 136a, 136b, 136c is reduced. Similarly, if information such as an algorithm for determining a prescription or new lens data is generated or updated, only the central calculation computer 142 would require an update rather than each of the ordering computers 136a, 136b, 136c requiring an update.

Figure 4:
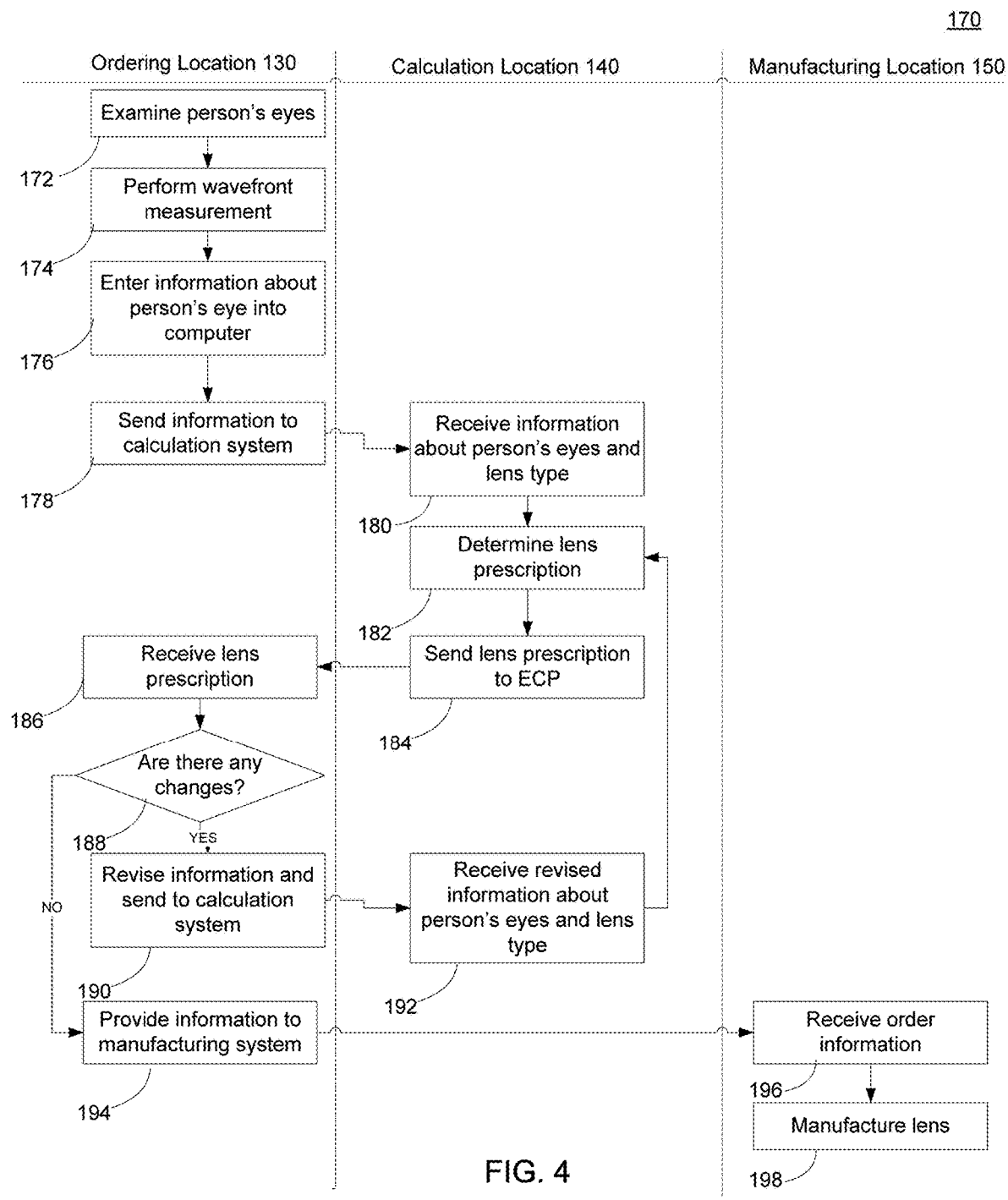
FIG. 4 is a flow chart showing a procedure for determining an eyeglass prescription and ordering lenses.

FIG. 4 shows a process 170 for using the ordering computer 136, calculation computer 142 and manufacturing computer 152 to generate and place an order for eyeglass lenses. Portions of the process 170 occur at each of the ordering location 130, the calculation location 140, and the manufacturing location 150 as indicated by the left, middle, and right vertical columns, respectively.

At the ordering location 130, the ECP 132 examines 172 the eyes of the person 134 (172). The examination can include making anamnesis (e.g., as shown in step 102 of FIG. 1). Making anamnesis typically involves questioning the person 134 regarding his or her medical and ocular history and any noticeable eye problems. Anamnesis can also include reviewing records of the person's eye care history. For example, in some embodiments, the anamnesis can be performed in conjunction with reviewing a previous eyeglass prescription. The examination can also include a medical investigation of a person performed by the ECP 132 (e.g., as shown in step 104 of FIG. 1). The medical examination can include determining visual acuity in each eye using the Snellen Chart, which consists of random letters of different sizes. The letters for normal vision (20/20) are ⅜-inch tall, viewed at 20 feet. In some embodiments, the medical investigation can include measuring the person's eye movement and peripheral vision. These can be tested by moving a light or object through the person's field of vision and observing the person's response. The person's reaction to light (e.g., pupillary response) can also be measured. The examination can also include testing color vision, contrast sensitivity and night vision.

During the examination, color blindness can be tested by, for example, having the person observe multicolored dots that form numbers. Color blindness can result in the person's inability to see certain numbers or to see a different number than people who are not color blind. The medical examination can also include glaucoma testing (e.g., tonometry), which typically involves directing a puff of air at the person's eye. The eye's response to the air puff is used to measure the pressure of the person's eyes, where abnormal readings are related to glaucoma. The medical investigation also generally includes visual observation of the person's eyes by the ECP 132. For example, the retina, fundus, retinal vessels, and optic nerve head can be viewed with an ophthalmoscope. Drops that dilate the person's pupil may be used to allow more of the fundus to be viewed, although subjective refractive is generally performed prior to this dilation as these drops typically blur the person's vision for a period of time.

The examination can also include subjective refraction analysis, sometimes referred to simply as a refraction (e.g., as shown in step 106 of FIG. 1). Subjective refraction generally involves positioning different lenses of different strength in front of the person's eyes using a phoropter or a trial frame and asking the person about their vision for the different lenses. Typically, the person sits behind the phoropter, and looks through it at an eye chart placed at optical infinity (e.g., 20 feet or 6 meters for distance vision), then at near (e.g., 16 inches or 40 centimeters for near vision) for individuals needing reading glasses. The ECP 132 then changes lenses and other settings, while asking the person for subjective feedback on which settings gave the best vision. Subjection refraction is typically performed on each eye separately (monocular refraction), and then on both eyes together (binocular refraction). In certain embodiments, subjective refraction is performed only on both eyes together to provide binocular information. In such cases, the monocular information is determined from wavefront measurement. Subjective refraction can be used to determine initial values for sphere (also referred to as mean sphere), cylinder, and/or cylinder axis for both eyes. Also, in some embodiments, subjective refraction can be used to determine prism and base. This information can be determined for both distance vision and near vision.

The process 170 also includes performing a wavefront measurement (174). The wavefront measurement can be performed using a Hartmann-Shack sensor. In such sensors, a narrow beam of radiation output from a laser or a superluminescence diode, for example, is projected onto the retina of the person's eye through the optics of the eye. Then, radiation scattered from the retina passes through the optics, and emerges from the pupil. The wavefront of the emerging beam carries information relating to aberration errors of the optics of the eye. Then, the wavefront of the emerging beam at the exit pupil plane of the eye is relayed (by relay optics) onto a Hartmann-Shack sensor, and output from the Hartmann-Shack sensor is used to measure the wavefront of the emerging beam. For an emmetropic eye, i.e., an eye without aberration error, the wavefront of the emerging beam is a flat surface, whereas, for an eye that produces aberration errors, the wavefront of the emerging beam is distorted from the flat surface.

A Hartmann-Shack sensor typically includes a lenslet array and a CCD camera, which CCD camera is typically located at a focal plane of the lenslet array. Whenever a beam to be measured is projected onto the Hartmann-Shack sensor, the lenslet array breaks the beam into sub-apertures, and forms a pattern of focal spots. The CCD camera records this pattern of focal spots, and a computer analyzes the pattern of focal spots to measure the wavefront of the beam.

Further embodiments of methods and systems for making wavefront measurements of a people eyes are disclosed in the following patents: U.S. patent application Ser. No. 11/835,109, entitled "EYEGLASS PRESCRIPTION METHOD" and filed on Aug. 7, 2007; U.S. Pat. No. 6,382,795 B1, entitled "METHOD AND APPARATUS FOR MEASURING REFRACTIVE ERRORS OF AN EYE;" U.S. Pat. No. 6,406,146 B1, entitled "WAVEFRONT REFRACTOR SIMULTANEOUSLY RECORDING TWO HARTMANN-SHACK IMAGES;" U.S. Pat. No. 6,575,572 B2, entitled "METHOD AND APPARATUS FOR MEASURING OPTICAL ABERRATIONS OF AN EYE;" U.S. Pat. No. 6,997,555 B2, entitled "METHOD FOR DETERMINING VISION DEFECTS AND FOR COLLECTING DATA FOR CORRECTING VISION DEFECTS OF THE EYE BY INTERACTION OF A PATIENT WITH AN EXAMINER AND APPARATUS THEREFORE;" and U.S. Pat. No. 7,084,986 B2, entitled "SYSTEM FOR MEASURING THE OPTICAL IMAGE QUALITY OF AN EYE IN A CONTACTLESS MANNER." The entire contents of U.S. Ser. No. 11/835,109, U.S. Pat. No. 6,382,795 B1, U.S. Pat. No. 6,406,146 B1, U.S. Pat. No. 6,575,572 B2, U.S. Pat. No. 6,997,555 B2, and U.S. Pat. No. 7,084,986 B2 are hereby incorporated herein by reference.

The wavefront refractor can measure a variety of different optical errors of the person's eyes, such as, for example, second order aberrations, defocus, astigmatism, and higher order aberrations including coma, trefoil, and spherical aberrations. These errors can be measured quickly (e.g., in seconds).

After collecting the information from the eye examination and the wavefront measurement, the ECP 132 enters information about the patient's eyes into the ordering computer 136 at the ordering location 130 (176). This information is sent from the ordering computer 136 to the calculation computer 142 (178). In addition to the examination and wavefront information, the information sent to the calculation computer 142 can include information about the eyeglass frames and centration measurement. Centration refers to the horizontal distance between the centration points of the pair of lenses and can be specified by monocular values, measured from the assumed centreline of the bridge of the nose or spectacle frame. Alternatively, if an inter-pupillary distance is specified, this is taken to be the centration distance. In certain embodiments, additional features for the eye glasses, for example, optional optical coatings (e.g., antireflection coatings), bifocal lenses, and/or sun-activated tints can also be entered into the ordering computer 136 and sent to the calculation computer 142.

The calculation computer 142 receives the information from the ordering computer 136 (180) and determines the person's prescription based on the results of subjective refraction and wavefront measurement using an algorithm (182). In general, the algorithm can utilize data from a number of different sources to calculate the person's prescription. For example, in certain embodiments, the algorithm takes into account the wavefront data from both eyes, the data from subjective refraction from both eyes, and additional data from the ECP 132. Additional data can include, for example, addition, prism, and/or base for one or both eyes, design preferences, and/or expected light conditions for the use one or both lenses. Another example of additional data is where the ECP 132 wants the prescription to be optimized for a certain distance (e.g., different from infinity), this information can be provided so that subsequent determinations are performed based on the distance.

In some embodiments, the calculation computer 142 determines the person's prescription from wavefront data by first determining Zernike coefficients which characterize the aberrations in the person's eye. Alternatively, or additionally, the person's prescription can be calculated from the three-dimensional wavefront map itself. The person's prescription (e.g., sphere, cylinder, and cylinder axis) can be determined from the Zernike coefficients or from the three-dimensional map using a variety of methods. For example, one can calculate sphere, cylinder, and cylinder axis by fitting a torical surface to the wavefront data. Alternatively, or additionally, the Zernike coefficients or the three-dimensional wavefront map can be used to construct an image of a point source on the person's retina, and the sphere, cylinder, and cylinder axis can be determined using an image quality metric.

In some embodiments, the calculation computer 142 determines the person's prescription from wavefront data for distance vision and wavefront data for near vision. With this, the person's prescription can be calculated including both the prescription for distance vision and the prescription for near vision.

Exemplary methods are disclosed, for example, in U.S. Pat. No. 6,511,180, entitled "DETERMINATION OF OCULAR REFRACTION FROM WAVEFRONT ABERRATION DATA AND DESIGN OF OPTIMUM CUSTOMIZED CORRECTION," and in European Patent No. EP 1 324 689 B1, entitled "DETERMINATION OF OCULAR REFRACTION FROM WAVEFRONT ABERRATION DATA," the entire contents both of which is hereby incorporated by reference.

In some embodiments, the calculation computer 142 determines the person's prescription from wavefront data using ray tracing techniques. For example, a ray tracing algorithm can be used to trace a bundle of rays through the patient's eye based on the wavefront data. Sphere, cylinder, and cylinder axis, for example, can be determined from the behavior of the rays at various locations along their path using one or more metrics. For example, in some embodiments, the prescription is determined using a metric based on characteristics of the bundle of rays at and around their point of minimum aperture (e.g., at their position of focus within the eye). These characteristics can include the cross-sectional area, cross-sectional shape, and/or longitudinal extension at this position.

Figure 5:
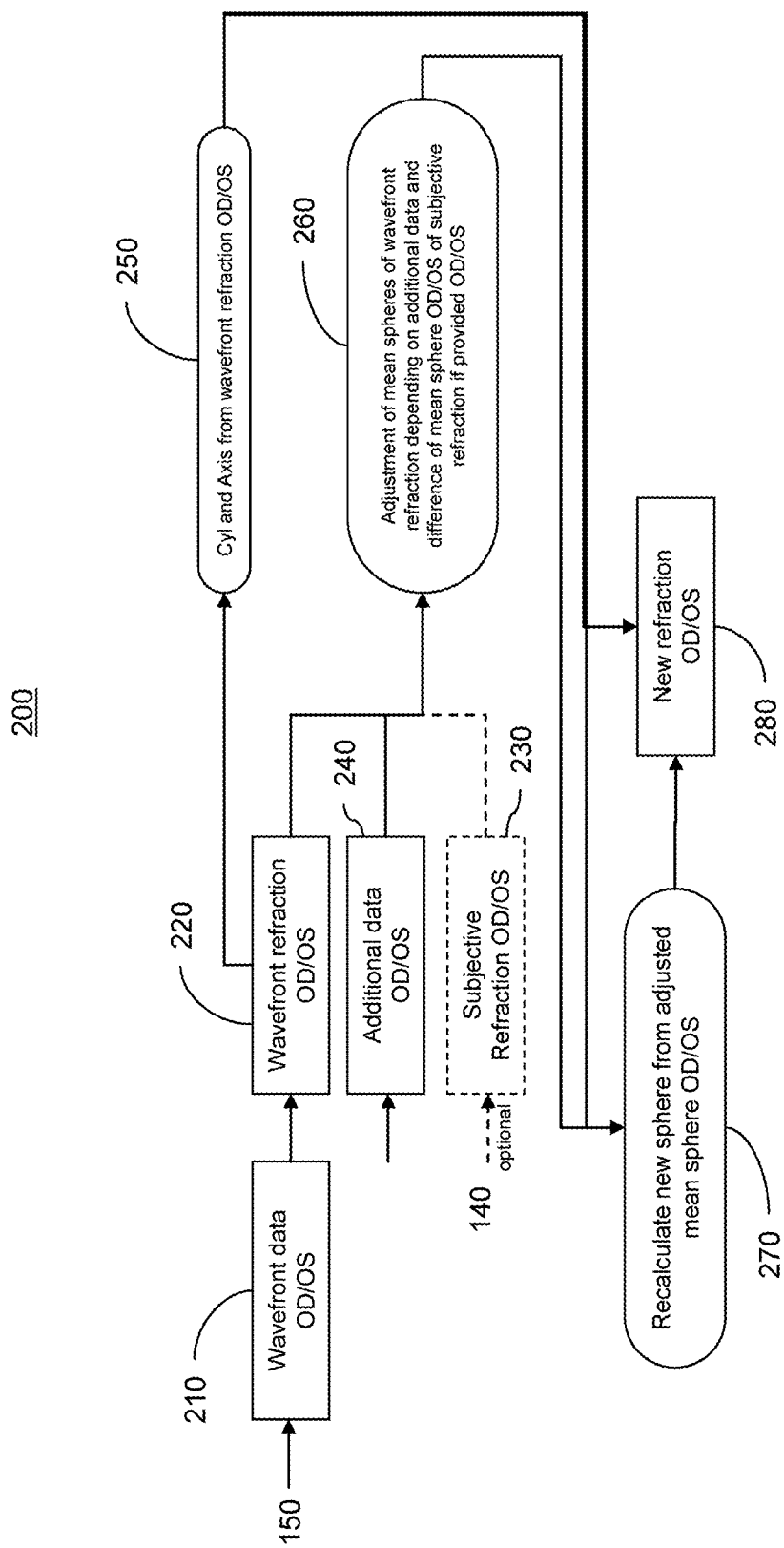
FIG. 5 is a flow chart showing a procedure for determining an eyeglass prescription.

FIG. 5 shows a flowchart of an exemplary embodiment of an algorithm for calculating a person's eyeglass prescription. Initially, wavefront data (210) for each eye, provided by wavefront measurement 150, is used to determine a wavefront refraction for each eye (220). This involves the use of an appropriate metric on the wavefront data. The metric depends on the wavefront data, the subjective refraction (if provided) and/or the additional data. Wavefront refraction data for each eye is used to determine a cylinder and cylinder axis for each eye (250). The cylinder refers to a cylindrical deviation from a spherical lens that part of a person's prescription, usually used to correct for astigmatism. The cylinder axis refers to the relative orientation of the cylinder for each eye. Concurrently to determining the cylinder and cylinder axis, the mean spheres of wavefront refraction for each eye is adjusted (260) based on the wavefront refraction data, subjective refraction data 230 and/or additional data 240 for each eye. For example, if ECP 132 had to adjust the mean sphere ascertained from subjective refraction 140 for one eye, this adjustment can be emulated by adjusting the wavefront refractive mean sphere of the other eye by a certain amount the difference between the mean sphere for the left eye is the same as the right eye as calculated from subjective refraction 140 is the same as the difference calculated from wavefront refraction 150.

Once appropriate mean sphere adjustments are calculated, new mean sphere values are determined from the adjustments (270). The adjusted mean sphere values are combined with the cylinder and cylinder axis calculated in step 250 to determine the prescription for the person (280).

In general, the person's eyeglass prescription can be determined to a high level of accuracy using the procedures presented herein. For example, spherical and cylinder can be determined to within about 0.25 dpt or less (e.g., about 0.1 dpt or less, about 0.05 dpt or less, 0.01 dpt or less). Cylinder axis can be determined to within about ±5° or less (e.g., about ±4° or less, about ±3° or less, about ±2° or less, ±1° or less).

Referring back to FIG. 4, after determination of the lens prescription is complete, the calculation computer 142 sends the lens prescription data to the ECP 132 (184). The ordering computer 136 receives the lens prescription data (186) and the ECP 132 reviews the prescription. The ECP 132 determines if any changes are desired and/or needed to the prescription (188). If the ECP 132 decides to make changes to the prescription or to other features of the lenses (e.g., the material, the coatings, the eyeglass frame), the ECP 132 revises the information in the ordering computer 136 and the ordering computer sends the revised information to the calculation computer 142 (190). The calculation computer 142 receives the information (192) and re-determines the lens prescription (182) and sends the lens prescription to the ordering computer (184).

After all selections have been made and the ECP 132 is satisfied with the prescription, the ECP 132 orders the lenses from the manufacturing location 150, e.g., a third party or in-house lens maker. In order to place the order for the lenses, the ordering computer 136 transfers information needed to generate the lens to the manufacturing computer 152 (194). This information includes the prescription information for the lenses and information about the materials used to create the lens. Since the calculations to generate the lens prescription based on the information from the ECP's examination of the patient's eyes and the wavefront measurements were performed using the calculation computer 142, it is not necessary to transfer the wavefront measurements to the manufacturing computer 152. The manufacturing computer 152 receives the order information (196) and manufactures the lenses according to the order information (198).

Figure 6:
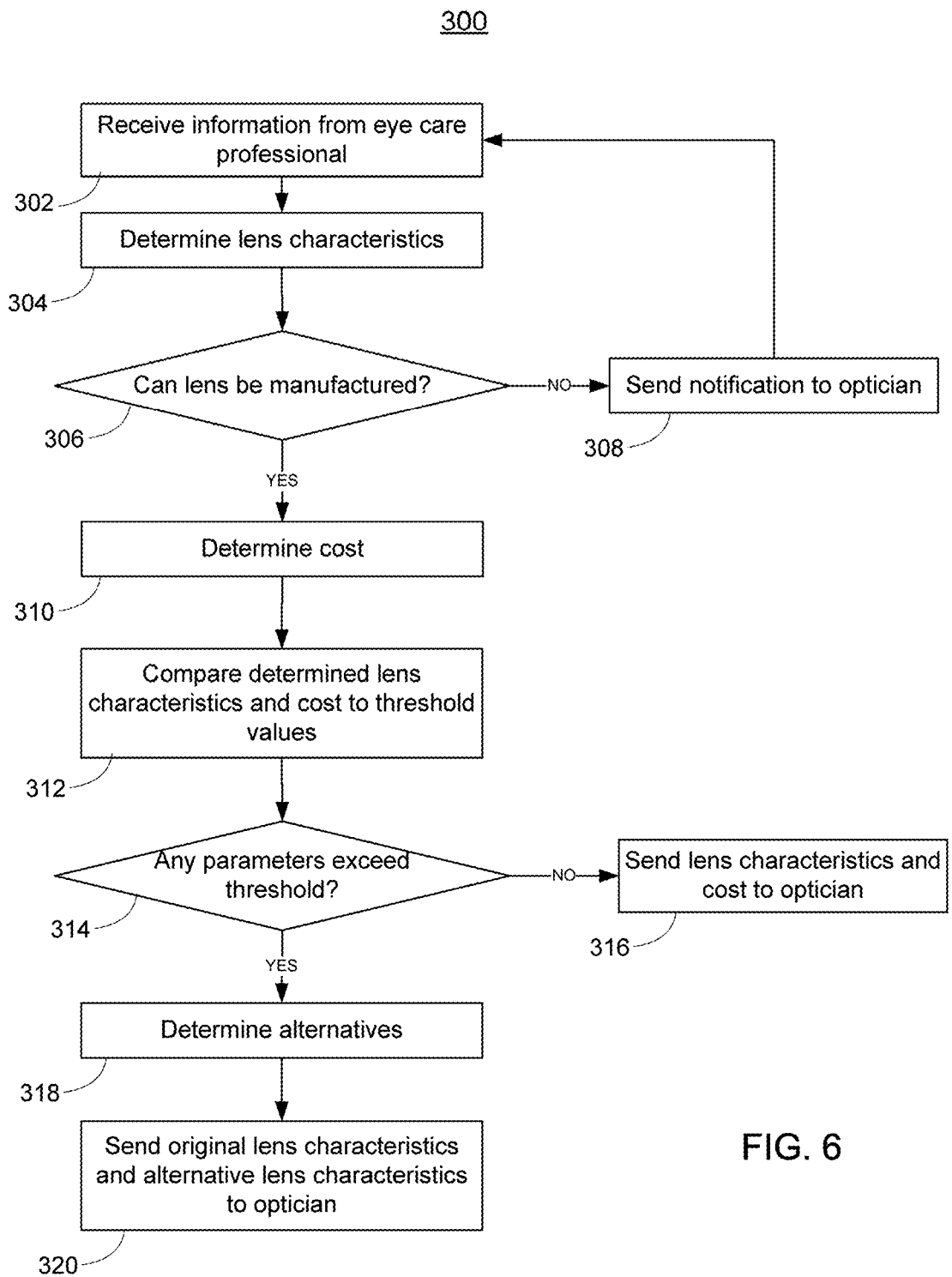
FIG. 6 is a flow chart showing a procedure for determining an eyeglass prescription.

The process of determining the lens prescription and lens characteristics can be an iterative process where the ECP 132 submits information to the calculation computer 142, receives lens prescription and lens characteristics, and revises the information based on the received lens prescription and lens characteristics. FIG. 6 shows an exemplary process 300 for determining lens characteristics based on factors such as prescription, manufacturability, cost, weight, coatings, and/or lens thickness. Since the calculations for determining the lens prescription and lens characteristics are performed at a location other than the manufacturing site (e.g., on the calculation computer 142), the ECP 132 can revise the prescription in such an iterative process prior to placing an order for the lenses.

In process 300, shown in FIG. 6, the calculation computer 142 receives information from the ECP 132 (302) and determines lens characteristics including the lens prescription (304). For example, the calculation computer can determine the lens prescription and characteristics using one or more of the processes described herein. Based on the calculated lens prescription and characteristics, the calculation computer 142 determines whether the lens can be manufactured (306). If the lens can not be manufactured, the calculation computer 142 sends a notification to the ECP 132 (308). The ECP 132 revises the information sent to the calculation computer 142 and the calculation computer 142 determines a revised lens prescription and characteristics (304). If the lens is capable of being manufactured, the calculation computer 142 determines an estimated cost for manufacturing the lenses (310). The cost can be based on the type of material selected for the lens, the shape of the lens, the coating on the lens, and/or the prescription. The calculation computer compares the estimated cost and the lens characteristics to pre-set threshold values (312). The threshold values can be set by the ECP 132 at the time the information is sent to the calculation computer 142 or can be predetermined and stored in the calculation computer 142. For example, threshold values can be set for the maximum thickness of the lens, maximum weight of the lens, and/or maximum price of the lens. If the determined lens characteristics do not exceed any of the thresholds, the lens prescription, lens characteristics, and estimated cost are sent to the ECP 132 (316). On the other hand, if one or more of the determined lens characteristics exceeds a threshold, the calculation computer determines alternatives for the lens (318). For example, if the cost of the lens exceeds the maximum price threshold, the calculation computer can suggest an alternative material for fabrication of the lens. In another example, if the lens weight exceeds a weight-based threshold, the calculation computer can suggest an alternative, lighter material for manufacturing the lens. After the calculation computer determines alternatives (318), the original lens prescription, lens characteristics, and estimated cost and the alternative lens prescription, lens characteristics, and estimated cost are sent to the ECP 132 (320). After receiving the information about the lens prescription, lens characteristics, and estimated cost, the ECP 132 reviews the information and determines whether to order the lenses.

In some embodiments, the wavefront measurement can provide additional information about the person's vision. For example, wavefront measurement 150 can be used to provide information about the person's night vision. Furthermore, a corneal topography measurement can be made concurrently to the wavefront measurement 150, in order to determine additional information about the refractive status of the eye, which can also be used in the calculation of the eyeglass prescription. The topographic information can also be used, for example, to dispense contact lenses.

The additional information (e.g., about night vision) can be obtained from the same wavefront measurement used to obtain prescription information. Accordingly, this information can be obtained without further stressing or inconveniencing the person.

While in at least some of the embodiments described herein, connections were described between the order computer 132 and the calculation computer 142 and between the order computer 132 and the manufacturing computer 152, in some embodiments additional or alternative connections could exist. For example, in some embodiments, there could additionally be a direct link between the calculation computer 142 and the manufacturing computer 152. For example, an ECP could enter information into the order computer 132 and use the calculation computer 142 to perform the calculations to determine the characteristics of the lens. After the ECP approved the determined characteristics of the lens, the order computer 132 could transmit a command to the calculation computer 142. Upon receipt of the command the calculation computer 142 could send the information for manufacturing the lens to the manufacturing computer 152.

The systems (e.g., the order computer 132, the calculation computer 142, and the manufacturing computer 152) and methods described herein can be implemented in digital electronic circuitry, or in computer hardware, firmware, software, web-enabled applications, or in combinations thereof. Data structures used to represent information provided can be stored in memory and in persistence storage. Apparatus of the invention can be implemented in a computer program product tangibly embodied in a machine-readable storage device for execution by a programmable processor and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired, and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files, such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

What is claimed is:

1. A method for dispensing eyeglasses comprising:
   receiving information about a person's vision including information from an eye examination and a wavefront measurement and a lens to be manufactured at a second computer;
   determining initial lens characteristics based on the information about the person's vision and the lens to be manufactured with the second computer;
   determining whether the lens can be manufactured based on the initial lens characteristics with the second computer;
   determining alternative lens characteristics if the lens cannot be manufactured based on the initial lens characteristics with the second computer;
   sending a notification from the second computer to a first computer whether the lens can be manufactured, the first computer being located at an eye care professional's office;
   sending at least one of the initial lens characteristics or the alternative lens characteristics from the second computer to the first computer, for the purpose of sending an order for a lens based on either the initial lens characteristics or the alternative lens characteristics by the first computer to a third computer, the third computer being located at a manufacturing site; and
   calculating, by the second computer, the order for the lens containing prescription information including sphere, cylinder, and cylinder axis based on the wavefront measurement.

2. The method according to claim 1, wherein the information about the lens to be manufactured includes at least one of a lens material, a coating, or an eyeglass frame.

3. The method according to claim 1, wherein the initial lens characteristics and/or the alternative lens characteristics include at least one of a prescription, a manufacturability, a cost, a weight, a material, a coating, or a lens thickness.

4. The method according to claim 1, further comprising:
   receiving revised information about the person's vision and/or the lens to be manufactured at the second computer;
   determining whether the lens can be manufactured based on the revised information about the person's vision and/or the lens to be manufactured with the second computer; and
   determining further alternative lens characteristics if the lens cannot be manufactured based on the revised information about the person's vision and/or the lens to be manufactured with the second computer.

5. The method according to claim 1, wherein the information about the person's vision comprises objective refraction data derived from one or more wavefront measurements.

6. The method according to claim 5, further comprising:
   calculating the lens prescription for the person based on the wavefront data with the second computer; and
   sending the calculated lens prescription to the first computer.

7. The method according to claim 5, wherein the information about the person's vision further comprises subjective refraction data.

8. The method according to claim 7, wherein the objective refraction data is derived for both eyes of the person, and wherein mean spheres derived from the wavefront measurement for each eye are adjusted based on subjective refraction data and/or additional data for each eye.

9. The method according to claim 8, wherein a mean sphere derived from subjective refraction of one eye is adjusted, wherein the mean sphere derived from objective refraction of the other eye is emulated by adjusting the mean sphere of the other eye by a same amount than the adjustment of the mean sphere derived from subjective refraction.

10. The method according to claim 9, wherein the prescription is determined from the adjusted mean sphere values combined with values for cylinder and cylinder axis.

11. A computer being configured to:
    receive information about a person's vision including information from an eye examination and a wavefront measurement and a lens to be manufactured;
    determine initial lens characteristics based on the information about the person's vision and the lens to be manufactured;
    determine whether the lens can be manufactured based on the initial lens characteristics; determine alternative lens characteristics if the lens cannot be manufactured based on the initial lens characteristics;
    send a notification to a first computer whether the lens can be manufactured, the first computer being located at an eye care professional's office; and
    send at least one of the initial lens characteristics or the alternative lens characteristics to the first computer, for the purpose of sending an order for a lens based on either the initial lens characteristics or the alternative lens characteristics by the first computer to a third computer, the third computer being located at a manufacturing site; and
    calculate, with the second computer, the order for the lens containing prescription information including sphere, cylinder, and cylinder axis based on the wavefront measurement.

12. The computer according to claim 11, further being configured to:
    determine an estimated cost for manufacturing the lens based on at least one of a type of material selected for the lens, a shape of the lens, a coating on the lens, or a prescription.

13. The computer according to claim 11, further being configured to:
    compare the initial lens characteristics to a pre-set threshold value selected from at least one of a maximum thickness of the lens, a maximum weight of the lens, or a maximum price of the lens.

14. The computer according to claim 11, further being configured to:
    receive revised information about the person's vision and/or the lens to be manufactured, determine whether the lens can be manufactured based on the revised information about the person's vision and/or the lens to be manufactured, and determine further alternative lens characteristics if the lens cannot be manufactured based on the revised information about the person's vision and/or the lens to be manufactured.

15. The computer according to claim 11, wherein the information about the person's vision comprises objective refraction data derived from one or more wavefront measurements.

16. The computer according to claim 15, further being configured to:
calculate the lens prescription for the person based on the wavefront data; and send the calculated lens prescription to the first computer.

17. The computer according to claim 15, wherein the information about the person's vision further comprises subjective refraction data.

18. The computer according to claim 17, wherein the objective refraction data is derived for both eyes of the person, and wherein mean spheres derived from the wavefront measurement for each eye are adjusted based on subjective refraction data and/or additional data for each eye.

19. The computer according to claim 18, wherein a mean sphere derived from subjective refraction of one eye is adjusted, and wherein the mean sphere derived from objective refraction of the other eye is emulated by adjusting the mean sphere of the other eye by a same amount than the adjustment of the mean sphere derived from subjective refraction.

20. The computer according to claim 19, wherein the prescription is determined from the adjusted mean sphere values combined with values for cylinder and cylinder axis.

* * * * *

UNITED STATES PATENT AND TRADEMARK OFFICE
CERTIFICATE OF CORRECTION

| | | |
|---|---|---|
| PATENT NO. | : 12,014,332 B2 | |
| APPLICATION NO. | : 18/047686 | |
| DATED | : June 18, 2024 | |
| INVENTOR(S) | : Timo Kratzer et al. | |

It is certified that error appears in the above-identified patent and that said Letters Patent is hereby corrected as shown below:

In the Specification

In Column 1, Line 12: change "both" to -- all --

In Column 9, Line 43: change "can not" to -- cannot --

Signed and Sealed this
Twenty-third Day of July, 2024

Katherine Kelly Vidal
*Director of the United States Patent and Trademark Office*